United States Patent

Shimizu et al.

[11] Patent Number: 4,737,506
[45] Date of Patent: Apr. 12, 1988

[54] ANTI-ARTERIOSCLEROTIC PYRIDYL OR IMIDAZOLYL DERIVATIVES OF CARBONYLOXYALKYL HANTZSCH ESTERS

[75] Inventors: Noboru Shimizu; Hiroyuki Ishiwata, both of Higashimurayama; Tomio Ohta, Sayama; Hiroshi Ishihama, Higashimurayama; Yasumi Uchida, Ichikawa, all of Japan

[73] Assignee: Kowa Co., Ltd., Nagoya, Japan

[21] Appl. No.: 851,134

[22] PCT Filed: Aug. 12, 1985

[86] PCT No.: PCT/JP85/00449

§ 371 Date: Apr. 7, 1986

§ 102(e) Date: Apr. 7, 1986

[87] PCT Pub. No.: WO86/01206

PCT Pub. Date: Feb. 27, 1986

[30] Foreign Application Priority Data

Aug. 14, 1984 [JP] Japan .................. 59-169588

[51] Int. Cl.[4] .................. A61K 31/455; C07D 401/12
[52] U.S. Cl. .................. 514/332; 514/333; 514/341; 546/256; 546/257; 546/258; 546/263; 546/278
[58] Field of Search .............. 546/278, 256, 257, 258, 546/263; 514/332, 333, 341

[56] References Cited

U.S. PATENT DOCUMENTS 4,656,181  4/1987  Sunkel et al. .................. 546/321

FOREIGN PATENT DOCUMENTS 0215684  10/1985  Japan .................. 546/278

OTHER PUBLICATIONS

Derwent Abstract 85-307998/49.

Primary Examiner—Henry R. Jiles
Assistant Examiner—Dale A. Bjorkman
Attorney, Agent, or Firm—Oblon, Fisher, Spivak, McClelland & Maier

[57] ABSTRACT

This invention relates to a 1,4-dihydropyridine-3,5-dicarboxylate derivative represented by the following general formula (I):

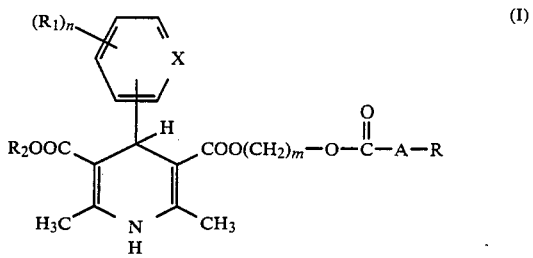

wherein R means an imidazolyl or pyridyl group, $R_1$ denotes a hydrogen or halogen atom or a nitro or trifluoromethyl group, $R_2$ is a lower alkyl group, X is CH or N, A means a lower alkylene group,

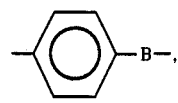

B being a lower alkylene or O-lower alkylene group,

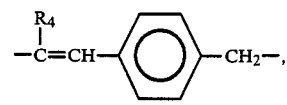

$R_4$ being a hydrogen atom or lower alkyl group, or

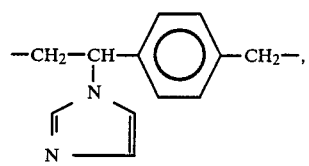

m denotes a number of 1–3, and n stands for 1 or 2. The derivative has vasodilative effects, hyperkinemic effects, platelet aggregation inhibitory effects, thromboxane $A_2$ formation inhibitory effects and so on, and are hence useful as a pharmaceutical product such as vasodilator, antihypertensive, antithrombotic agent, antiarteriosclerotic agent or the like.

3 Claims, No Drawings

ANTI-ARTERIOSCLEROTIC PYRIDYL OR IMIDAZOLYL DERIVATIVES OF CARBONYLOXYALKYL HANTZSCH ESTERS

TECHNICAL FIELD

This invention relates to novel 1,4-dihydropyridine-3,5-dicarboxylate derivatives, and more specifically to 1,4-dihydropyridine-3,5-dicarboxylate derivatives each of which is represented by the following general formula (I):

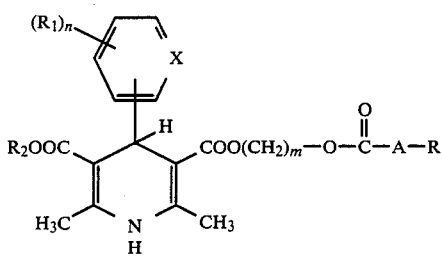

wherein R means is imidazolyl or pyridyl group, $R_1$ denotes a hydrogen or halogen atom or a nitro or trifluoromethyl group, $R_2$ is a lower alkyl group, X is CH or N, A means a lower alkylene group,

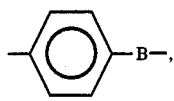

B being a lower alkylene or O-lower alkylene group,

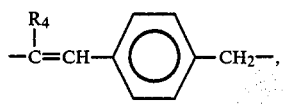

$R_4$ being a hydrogen atom or lower alkyl group, or

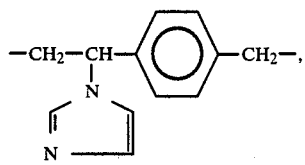

m denotes a number of 1-3, and n stands for 1 or 2.

BACKGROUND ART

It has already been known that certain derivatives of 1,4-dihydropyridine-3,5-dicarboxylic acid have pharmacological effects such as vasodilative effects. A variety derivatives of 1,4-dihydropyridine-3,5-dicarboxylic acid have heretofore been synthesized, pharmacological effects of which have also been studied. For example, nifedipine [Vater, W. et al, Arzneim. Forsch., 22, 1(1972)] and nicardipine [Takenaka, T. et al, Arzneim. Forsch., 26, 2172(1976)] have already been put as pharmaceutical products on the market.

These conventional derivatives of 1,4-dihydropyridine-3,5-dicarboxylic acid are however not fully satisfactory. There is thus an outstanding demand for the development of derivatives having still better pharmacological effects.

SUMMARY OF THE INVENTION

The present inventors have carried out an extensive research under the above-described circumstances. As a result, it has been found that the novel 1,4-dihydropyridine-3,5-dicarboxylate derivatives represented by the general formula (I) have excellent pharmacological effects.

Namely, the compounds (I) of this invention have vasodilative effects, hyperkinemic effects, platelet aggregation inhibitory effects, thromboxane $A_2$ formation inhibitory effects and so on, and are hence useful as pharmaceutical products such as vasodilators, antihypertensives, antithrombotic agents, anti-arteriosclerotic agents, etc. The compounds (I) of this invention are advantageous particularly as therapeutic agents for arteriosclerosis as they have both coronary hyperkinemic effects and thromboxane $A_2$ formation inhibitory effects. In addition, compared with the above-mentioned nifedipine and nicardipine, the compounds (I) of this invention have such advantageous features that they show hyperkinemic effects for the coronary artery and vertebral artery over longer periods of time and weaker heart-beat increasing effects.

The compounds (I) of this invention can be prepared, for example, in accordance with any one of the following Processes A–D:

Process A

Using the Hantzsch Pyridine Synthesis [Annalen der Chemie, 215, 1, 72(1882)] or its modified process, the compounds (I) of this invention can be prepared in accordance with the following reaction scheme, in which all symbols have the same meaning as defined above.

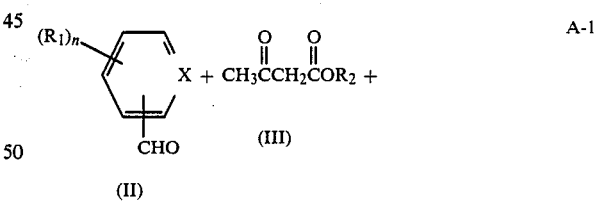

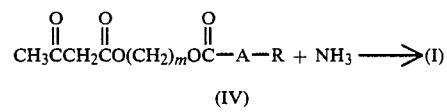

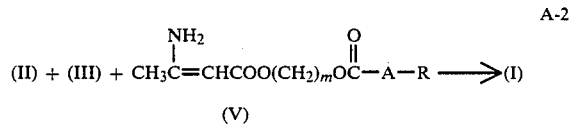

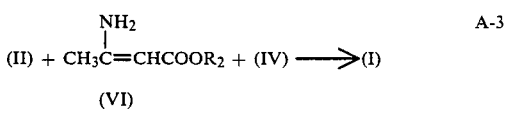

-continued

A-4

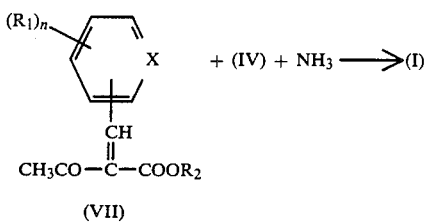
(VII)

(VII) + (V) ⟶ (I)　A-5

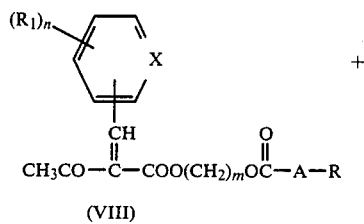
(VIII)

(III) + NH₃ ⟶ (I)　A-6

(VIII) + (VI) ⟶ (I)　A-7

Of the above-illustrated Processes A-1–A-7, A-1 is the Hantzsch Pyridine Synthesis while Processes A-2–A-7 are its modifications.

The reactions of Process A-1–A-7 may be effected by heating their respective reactants in a solvent or without using any solvent, at 30°–180° C. or preferably 50°–130° C. and for 2–24 hours. As the solvent, it is possible to use a lower alcohol such as ethanol, propanol, isopropanol or n-butanol, a halogenated hydrocarbon such as chloroform, dichloroethane or trichloroethane, benzene, pyridine or the like.

Process B

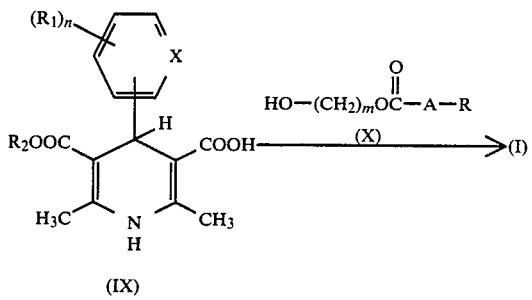
(IX)

By the reaction between the compound (IX) and the compound (X), the compound (I) of this invention can be prepared. This reaction may be carried out by reacting the compound (IX) with N,N'-carbonyldiimidazole and then with the compound (X), for example, in an inert solvent. Upon conducting this reaction, it is possible to use 1,8-diazabicyclo-[5.4.0]-7-undecene (hereinafter called "DBU"), sodium alcoholate, alkali metal imidazole or the like as a reaction accelerator. As the inert solvent, may be used tetrahydrofuran, dioxane, chloroform, methylene chloride, N,N-dimethylformamide, dimethyl sulfoxide, or the like. The reaction is allowed to proceed by stirring the reactants for 1–24 hours at room temperature or an elevated temperature, thereby to provide the compound (I).

Alternatively, the compound (I) may also be obtained by converting the compound (IX) into its corresponding acid halide in a manner known per se in the art and then reacting the acid halide further with the compound (X).

The compound (IX), one of the starting compounds, has already been known [Chem. Pharm. Bull., 27, 1426(1979)], and may be prepared by various processes.

Process C

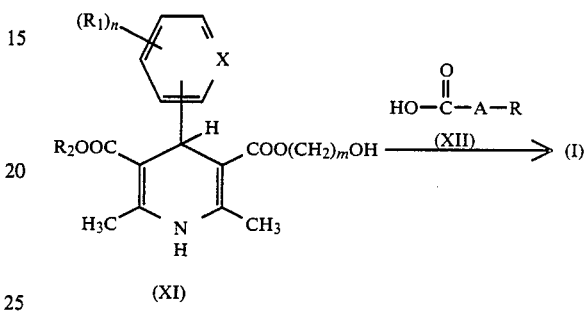
(XI)

By reacting the compound (XI) with the compound (XII), the compound (I) of this invention can be prepared. This reaction may be effected, for example, in an inert solvent and in the presence of a dehydrating agent such as dicyclohexylcarbodiimide (DCC) or the like. Upon conducting the reaction, it is feasible to use 4-dimethylaminopyridine, 4-pyrrolidinopyridine or the like as a reaction accelerator. Alternatively, it is also possible to react the compound (XI) with the imidazolide which has been obtained by reacting N,N'-carbonyldiimidazole with the compound (XII). In this case, the compound (I) is correspondingly obtained.

Incidentally, one of the starting compounds, the compound (XI), may be prepared in a manner similar to either one of the above-described Processes A-1, A-7. It may also be prepared by reacting the compound (IX) with a compound represented by the formula, HO—(CH₂)$_m$OH, in a manner similar to the above-described Process C.

Process D

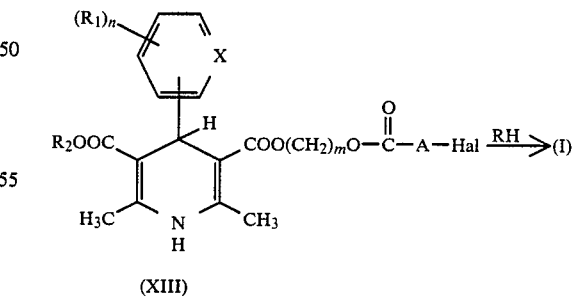
(XIII)

By causing the compound (XIII) to react with the imidazole or pyridine represented by the formula RH, the compound (I) of this invention is obtained. It is preferred to use imidazole as its alkali metal salt. On the other hand, it is preferred to use pyridine as pyridyl lithium, which is obtained for example by reacting n-butyl lithium with bromopyridine at −35° C., a pyridylalkyl lithium obtained in the same manner, or the like.

The reaction may advantageously proceed by carrying it out in an inert solvent, for example, ether or tetrahydrofuran, at a temperature of −80°−−30° C., for several minutes to 1 hour.

By the way, the starting compounds (XIII) for Process D may be prepared (1) in a manner similar to either one of the above-described Processes A-1-A-7, (2) by reacting the compound (IX) with a compound represented by the formula,

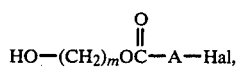

in a manner similar to Process B, or (3) by reacting the compound (XI) with a compound represented by the formula, HOCO—A—Hal, in a manner similar to Process C.

In the above-described Processes B-D, the compound (I) of this invention may also be obtained by using an N-protected compound of the compounds (IX), (XI) or (XIII) and, after effecting the corresponding reaction, by removing the protecting group. Here, as the protecting group, may be example be used a methoxymethyl group, ethoxymethyl group or the like. These protecting groups can be easily removed by hydrolysis or the like after completion of the reaction.

The thus-obtained compounds (I) of this invention may be converted, in accordance with methods known per se in the art, into their inorganic or organic acid salts such as hydrochlorides, hydrobromides, phosphates, sulfates, oxalates, acetates, citrates, maleates, tartrates, etc.

The followings are pharmacological effects of some representative compounds of this invention.

Using a ddY male mouse having a body weight of 35–40 g, one of the representative compounds of this invention was administered orally. One hour later, citrated blood was collected. PRP (platelet-rich plasma) was separated. Aggregation of platelets by the addition of 12.5 µg/ml of collagen was observed by an aggregometer. The amount of thromboxane $B_2$ (a stable metabolite of thromboxane $A_2$) formed 5 minutes later in the liquid reaction mixture was measured by the RIA method. Results are shown in Table 1, in terms of percent inhibition against the formation of thromboxane $B_2$ ($TXB_2$).

TABLE 1

| Compound | Dose (mg/kg) | Percent inhibition against $TXB_2$ formation (%) |
|---|---|---|
| Compound of Ex. 2 | 30 | 42 |
|  | 100 | 72 |
| Compound of Ex. 6 | 30 | 74 |
|  | 100 | 95 |
| Compound of Ex. 8 | 30 | 60 |
|  | 100 | 72 |
| Compound of Ex. 14 | 30 | 52 |
|  | 100 | 83 |
| Compound of Ex. 16 | 30 | 75 |
|  | 100 | 94 |

As shown in Table 1, the compounds of this invention have extremely strong thromboxane $A_2$ formation inhibitory effects.

The compounds of this invention have hyperkinemic effects for the coronary and vertebral arteries. Their advantageous feature is that they can show such effects over prolonged periods of time. Although they increase the amount of blood which flows through the coronary artery, they have another advantageous feature that they show weak heart-beat increasing effects.

These effects of the compounds of this invention indicate that they are useful not only as vasodilators but also as therapeutic drugs for arteriosclerosis.

When formulating the compounds of this invention into pharmaceutical compositions, liquid or solid carriers or diluents may be used. As these carriers, may be mentioned various excipients, binders, lubricants, emulsifiers, etc., which are by themselves known in the field of production of pharmaceutical compositions. Illustrative of carriers or diluents may include starches such as potato starch, wheat starch, corn starch and rice starch; saccharides such as lactose, sucrose, glucose, mannitol and sorbitol; celluloses such as crystalline cellulose, calcium carboxycellulose and moderately-substituted hydroxypropylcellulose; inorganic materials such as potassium phosphate, calcium sulfate, calcium carbonate and talc; binders such as gelatin, gum arabic, methylcellulose, sodium carboxymethylcellulose, polyvinyl pyrrolidone and hydroxypropylcellulose; anionic surfactants of the polyhydric alcohol ester type, such as fatty acid monoglycerides, sorbitan fatty acid esters, sucrose and polyglycerol fatty acid esters; anionic surfactants of the polyoxyethylene type; and so on.

These pharmaceutical compositions may be processed into any pharmaceutically-known dosable forms such as suppositories, powder, granules, tablets, troches, liquid preparations, injectable preparations, suspensions, etc.

Pharmaceutical compositions of the compounds of this invention may be administered in any route, namely, orally, or parenterally, e.g., intravenously, sublingually or via the rectum. Oral administration is however preferred when administered for long periods of time.

Dose may be subject to variations as needed. For example, the compounds (I) of this invention may each be administered at a dose of about 1–500 mg/body/day with 50–200 mg/body/day being preferred. The acute toxicity levels ($LD_{50}$) of the compounds of this invention are about 300 mg/kg (rat) when administered orally and 30–50 mg/kg (rat) when administered intravenously. Their toxicity levels are hence extremely low.

[EXAMPLES]

This invention will next be described by the following Examples.

EXAMPLE 1

3-Methyl 5-[2-[6-(1-imidazolyl)-hexanoyloxy]-ethyl]2,6-dimethyl-4-(3-nitrophenyl)-1,4-dihydropyridine-3,5-dicarboxylate (1) To an anhydrous N,N-dimethylformamide solution containing 170 mg of 6-bromohexanoic acid, 200 mg of N,N'-carbonyldiimidazole was added, and the resultant mixture was stirred at room temperature for 75 minutes.

To the reaction mixture, were then added an anhydrous N,N-dimethylformamide solution containing 323 mg of 3-methyl 5-(hydroxyethyl) 1-methoxymethyl-2,6-dimethyl-4-(3-nitrophenyl)-1,4-dihydropyridine-3,5-dicarboxylate and a solution which had been prepared by adding 116 mg of imidazole to an anhydrous N,N-dimethylformamide suspension containing 74 mg of 50% sodium hydride. The resultant mixture was stirred at room temperature for 19 hours.

After completion of the reaction, 50 ml of a saturated aqueous solution of ammonium chloride was added and the resultant mixture was extracted with ethyl acetate. The extract was successively washed first with a saturated aqueous solution of sodium hydrogencarbonate and then with a saturated brine, followed by its drying.

Upon purification of the residue, which had been obtained by distilling off the solvent, by silica gel column chromatography, 261 mg of 3-methyl 5-[2-[6-(1-imidazolyl)-hexanoyloxy]-ethyl]1-methoxymethyl-2,6-dimethyl-4-(3-nitrophenyl)-1,4-dihydropyridine-3,5-dicarboxylate was obtained as a light yellowish oily substance (yield: 58.1%).

IR $\nu_{max}^{film}$ cm$^{-1}$:
2936, 1735, 1695, 1640, 1526, 1348, 1212, 1155, 1070, 750

NMR δ (CDCl$_3$):

| | |
|---|---|
| 1.14–1.92 | (6H, m, —(CH$_2$)$_3$—) |
| 2.24 | (2H, t, J=7Hz, —CH$_2$COO) |
| 2.50 | (6H, s, —CH$_3$ × 2) |
| 3.28 | (3H, s, —OCH$_3$) |
| 3.66 | (3H, s, —COOCH$_3$) |
| 3.90 | (2H, t, J=7.2Hz, —CH$_2$—N imidazolyl) |
| 4.26 | (4H, s, —COOCH$_2$CH$_2$.OCO—) |
| 4.76 | (2H, s, >N—CH$_2$O—) |
| 5.12 | (1H, s, C$_4$—H) |
| 6.84, 6.92 | (1H × 2, s × 2, —N imidazolyl) |
| 7.82–8.04 | (2H, m, nitrophenyl H) |

(2) Dissolved in tetrahydrofuran was 344 mg of the above-obtained 1-methoxymethyl derivative, followed by an addition of 1.28 ml of 6N-hydrochloric acid. The resultant mixture was stirred at room temperature for 3.5 hours. After the reaction, the solvent was distilled off, a saturated aqueous solution of sodium hydrogencarbonate was added to the residue to make the residue alkaline, and the alkaline residue was then extracted with chloroform. The chloroform layer was separated, washed with water and then dried. The solvent was thereafter distilled off. The thus-obtained residue was purified by silica gel column chromatography, thereby obtaining 211 mg of 3-methyl 5-[2-[6-(1-imidazolyl)-hexanoyloxy]-ethyl]2,6-dimethyl-4-(3-nitrophenyl)-1,4-dihydropyridine-3,5-dicarboxylate as a light-yellowish viscous oily substance (yield: 66.3%).

IR $\nu_{max}^{liq.film}$ cm$^{-1}$;
3509, 3321, 3173, 2935, 1734, 1691, 1642, 1523, 1502, 1346, 1208, 1112, 745

NMR δ (CDCl$_3$):

| | |
|---|---|
| 1.10–1.90 | (6H, m, —(CH$_2$)$_3$—) |
| 2.27 | (2H, t, J=6.6Hz, —CH$_2$COO) |
| 2.34, 2.38 | (3H × 2, s × 2, —CH$_3$ × 2) |
| 3.66 | (3H, s, —COOCH$_3$) |
| 3.98 | (2H, t, J=6.6Hz, —CH$_2$—N imidazolyl) |
| 4.28 | (4H, s, —COOCH$_2$CH$_2$OCO—) |
| 5.12 | (1H, s, C$_4$—H) |
| 6.96, 7.08 | (1H × 2, s × 2, —N imidazolyl) |
| 7.52 | (1H, s, —N imidazolyl) |
| 7.68 | (1H, broad d, J=8Hz, nitrophenyl H) |
| 8.02 | (1H, broad d, J=8Hz, nitrophenyl H) |
| 8.15 | (1H, broad s, nitrophenyl H) |

EXAMPLE 2

3-Ethyl 5-[2-[4-[2-(1-imidazolyl)-ethoxy]-benzoyloxy]-ethyl]2,6-dimethyl-4-(3-nitrophenyl)-1,4-dihydropyridine-3,5-dicarboxylate Added to an anhydrous N,N-dimethylformamide solution containing 300 mg of 4-[2-(1-imidazolyl)ethoxy]-benzoic acid was 334 mg of N,N'-carbonyldiimidazole. The resultant mixture was stirred at room temperature for 100 minutes.

An anhydrous N,N-dimethylformamide solution containing 656 mg of 3-ethyl 5-(2-hydroxyethyl) 2,6-dimethyl-4-(3-nitrophenyl)-1,4-dihydropyridine-3,5-dicarboxylate and 236 mg of 1,8-diazabicyclo-[5.4.0]-7-undecene (DBU) was then added, and the resultant mixture was stirred for 13 hours.

After the reaction, 100 ml of a saturated aqueous solution of ammonium chloride was added and the resultant mixture was extracted with ethyl acetate. The ethyl acetate layer was separated, washed with a saturated brine, and then dried. The solvent was distilled off and the residue was purified by silica gel column chromatography to obtain 75 mg of 3-ethyl 5-[2-[4-[2-(1-imidazolyl)-ethoxy]-benzoyloxy]-ethyl]2,6-dimethyl-4-(3-nitrophenyl)-1,4-dihydropyridine-3,5-dicarboxylate as colorless amorphous powder (yield: 96.2%).

IR $\nu_{max}^{KBr}$ cm$^{-1}$:
3351, 2917, 1691, 1645, 1604, 1522, 1347, 1250, 1208, 1003, 766

NMR δ(CDCl$_3$):

| | |
|---|---|
| 2.16 | (3H, t, J=6Hz, —CH$_2$CH$_3$) |
| 2.32, 2.36 | (3H × 2, s × 2, —CH$_3$ × 2) |
| 4.06 | (2H, q, J=6Hz, —COOCH$_2$CH$_3$) |
| 4.20–4.60 | (8H, m, —COOCH$_2$CH$_2$OOC—, —OCH$_2$CH$_2$—N⟨imidazolyl⟩) |
| 5.10 | (1H, s, C$_4$—H) |
| 6.86 | (2H, d, J=9Hz, OOC—C$_6$H$_4$—) |
| 7.10 | (2H, s, —N⟨imidazolyl⟩) |
| 7.66 | (1H, s, —N⟨imidazolyl⟩) |
| 7.88 | (2H, d, J=9Hz, —C$_6$H$_4$—O—) |
| 8.10 | (1H, t, J=2Hz, nitrophenyl—H) |

EXAMPLE 3
3-Methyl 5-[2-[4-(1-imidazolylmethyl)benzoyloxy]-ethyl]2,6-dimethyl-4-(3-nitrophenyl)-1,4-dihydropyridine-3,5-dicarboxylate (1) Added to an anhydrous N,N-dimethylformamide solution containing 340 mg of 3-methoxycarbonyl-1-methoxymethyl-2,6-dimethyl-4-(3-nitrophenyl)-1,4-dihydropyridine-5-carboxylic acid was 220 mg of N,N'-carbonyldiimidazole. The resultant mixture was stirred at room temperature for 70 minutes. Then, an anydrous N,N-dimethylformamide solution containing 450 mg of hydroxyethyl 4-(1-imidazolylmethyl)-benzoate and 150 mg of DBU was added and the resultant mixture was stirred for 16 hours. After the reaction, 80 ml of a saturated aqueous solution of ammonium chloride was added and the resultant mixture was extracted with ethyl acetate. The ethyl acetate layer was separated, washed with a saturated brine, and then dried. The solvent was distilled off and the residue was purified by silica gel column chromatography to obtain 437 mg of 3-methyl 5-[2-[4-(1-imidazolylmethyl)-benzoyloxy]-ethyl]1-methoxymethyl-2,6-dimethyl-4-(3-nitrophenyl)-1,4-dihydropyridine-3,5-dicarboxylate as a light-yellowish viscous oily substance (yield: 80.0%).

IR $\nu_{max}^{liq.film}$ cm$^{-1}$:
3556, 3349, 3102, 2938, 1717, 1699, 1637, 1582, 1347, 1272, 1209, 1156, 1064, 740

NMR δ(CDCl$_3$):

| | |
|---|---|
| 2.50, 2.54 | (3H × 2, s × 2, —CH$_3$ × 2) |
| 3.32 | (3H, s, —OCH$_3$) |
| 3.66 | (3H, s, —COOCH$_3$) |
| 4.30–4.70 | (4H, m, —COOCH$_2$CH$_2$OOC—) |
| 4.82 | (2H, s, \N—CH$_2$—O) |
| 5.18 | (1H, s, C$_4$—H) |
| 5.20 | (2H, s, —CH$_2$—N⟨imidazolyl⟩) |
| 6.96 | (1H, s, —N⟨imidazolyl⟩ or —N⟨imidazolyl⟩) |
| 7.61 | (1H, s, —N⟨imidazolyl⟩) |

(2) Using 254 mg of the thus-obtained 1-methoxymethyl derivative, hydrolysis treatment and removal of the protecting group were effected in the same manner as in Example 1–2) to obtain 208 mg of 3-methyl 5-[2-[4-(1-imidazolylmethyl)-benzoyloxy]-ethyl]2,6-dimethyl-4-(3-nitrophenyl)-1,4-dihydropyridine-3,5-dicarboxylate as yellowish amorphous powder (yield: 91.6%).

IR $\nu_{max}^{KBr}$ cm$^{-1}$:
3319, 2918, 1722, 1688, 1523, 1348, 1270, 1209, 1090, 1015, 747

NMR δ(CDCl$_3$):

| | |
|---|---|
| 2.34, 2.38 | (3H × 2, s × 2, —CH$_3$ × 2) |
| 3.62 | (3H, s, —COOCH$_3$) |
| 4.20–4.60 | (4H, m, —COOCH$_2$CH$_2$OOC—) |
| 5.10 | (1H, s, C$_4$—H) |
| 5.21 | (2H, s, —CH$_2$—N⟨imidazolyl⟩) |
| 6.24 | (1H, broad s, \NH) |

| | |
|---|---|
| 6.96 | (1H, s, 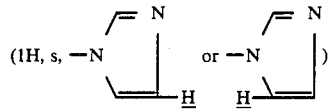) |
| 8.06 | (1H, broad s, 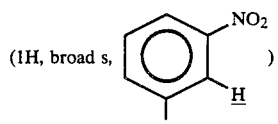) |

EXAMPLE 4

3-Methyl 5-[2-[3-[4-(1-imidazolylmethyl)phenyl]-acryloyloxy]-ethyl]2,6-dimethyl-4-(2-pyridyl)-1,4-dihydropyridine-3,5-dicarboxylate To an anhydrous N,N-dimethylformamide solution containing 200 mg of 4-(1-imidazolylmethyl)cinnamic acid, 213 mg of N,N'-carbonyldiimidazole was added. The resultant mixture was stirred at room temperature for 80 minutes.

An anhydrous N,N-dimethylformamide solution which contained 349 mg of 3-methyl 5-(2-hydroxyethyl)2,6-dimethyl-4-(2-pyridyl)-1,4-dihydropyridine-3,5-dicarboxylate and 147 mg of DBU was thereafter added. The resultant mixture was stirred for 13 hours. After adding 70 ml of a saturated aqueous solution of ammonium chloride to the reaction mixture, the reaction mixture was extracted with ethyl acetate. The ethyl acetate layer was washed with a saturated brine and then dried. The solvent was distilled off and the residue was purified by silica gel column chromatography. From a 50:2 mixed solvent of chloroform and methanol, 272 mg of 3-methyl 5-[2-[3-[4-(1-imidazolylmethyl)-phenyl]-acryloyloxy]-ethyl]2,6-dimethyl-4-(2-pyridyl)-1,4-dihydropyridine-3,5-dicarboxylate was obtained as yellowish amorphous powder (yield: 57.2%).

IR $\nu_{max}^{KBr}$cm$^{-1}$:
3332, 2940, 1689, 1635, 1498, 1306, 1209, 1114, 750

NMR δ(CDCl₃):

| | |
|---|---|
| 2.24, 2.28 | (3H × 2, s × 2, —C$\underline{H}_3$ × 2) |
| 3.60 | (3H, s, —COOC$\underline{H}_3$) |
| 4.20–4.50 | (4H, m, —COOC$\underline{H}_2$C$\underline{H}_2$OOC—) |
| 5.20 | (2H, s, —C$\underline{H}_2$—N 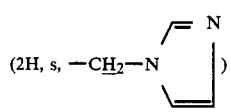) |
| 5.24 | (1H, s, C₄—$\underline{H}$) |
| 6.46 | (1H, d, J=16Hz, —C$\underline{H}$=C$\underline{H}$— 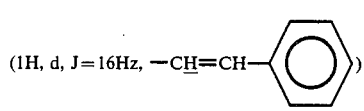) |
| 6.98 | (1H, s, —N 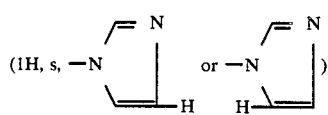) |

| | |
|---|---|
| 8.52 | (1H, broad d, J=4.8Hz, 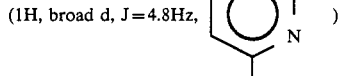) |
| 8.98 | (1H, broad s, 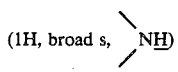) |

EXAMPLE 5

3-Methyl 5-[2-[3-(1-imidazolyl)-3-[4-(1-imidazolylmethyl)-phenyl]-propionyloxy]ethyl]2,6-dimethyl-4-(2-pyridyl)-1,4-dihydropyridine-3,5-dicarboxylate By using a 10:1 mixed solvent of chloroform and methanol upon conducting the purification by column chromatography in Example 4, 49 mg of the title compound was obtained as a yellowish viscous oily substance (yield: 9.2%).

IR $\nu_{max}^{liq.film}$cm$^{-1}$:
3260, 2943, 1735, 1685, 1500, 1431, 1213, 1114, 749

NMR δ(CDCl₃):

| | |
|---|---|
| 2.24, 2.26 | (3H × 2, s × 2, —C$\underline{H}_3$ × 2) |
| 3.20 | (2H, d, J=8Hz, 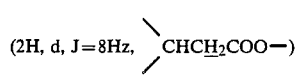CHC$\underline{H}_2$COO—) |
| 3.62 | (3H, s, —COOC$\underline{H}_3$) |
| 4.05–4.35 | (4H, m, —COOC$\underline{H}_2$C$\underline{H}_2$OOC—) |
| 5.14 | (2H, s, —C$\underline{H}_2$—N 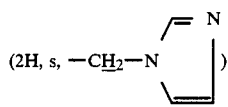) |
| 5.22 | (1H, s, C₄—$\underline{H}$) |
| 5.76 | (1H, t, J=8Hz, —CH₂—C$\underline{H}$—) 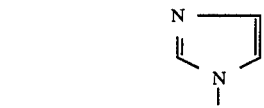 |
| 6.94, 6.98 | (1H × 2, broad s × 2, —N 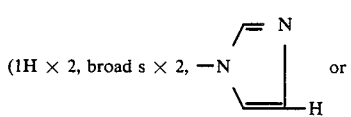 or —N 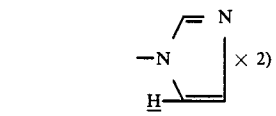 × 2) |
| 8.52 | (1H, broad d, J=8Hz, 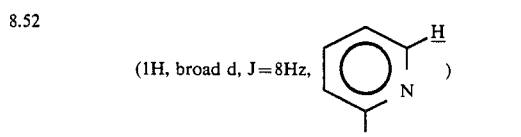) |

EXAMPLE 6

3-Ethyl 5-[3-[4-[2-(1-imidazolyl)ethoxy]benzoyloxy]propyl]2,6-dimethyl-4-(3-nitrophenyl)-1,4-dihydropyridine-3,5-dicarboxylate After adding 2.3 ml of thionyl chloride dropwise to 10 g of 2,6-dimethyl-3-ethoxycarbonyl-4-(3-nitrophenyl)-1,4-dihydropyridine-5-carboxylic acid in a mixed solvent consisting of 16 ml of anhydrous N,N-dimethylformamide and 52 ml of methylene chloride while maintaining the internal temperature below −5° C. with salt-ice cooling, the resultant mixture was stirred for 1 hour. Thereafter, while maintaining the internal temperature below −5° C., 7.54 g of 3-hydroxypropyl 4-[2-(1-imidazolyl)ethoxy]benzoate was added. The resulting mixture was stirred for 1 hour. Ice water was added to the reaction mixture, followed by an addition of an aqueous solution of sodium carbonate to make the mixture alkaline. The mixture was then extracted with chloroform. After washing the chloroform layer with water, the solvents were distilled off and the residue was purified by silica gel column chromatography to obtain 16 g of 3-ethyl 5-[3-[4-[2-(1-imidazolyl)ethoxy]benzoyloxy]propyl]2,6-dimethyl-4-(3-nitrophenyl)-1,4-dihydropyridine-3,5-dicarboxylate (yield: 90%).

Molecular formula:
$C_{32}H_{34}N_4O_9$
Appearance:
Yellowish powder
IR $\nu_{max}^{KBr}$cm$^{-1}$:
3319, 2934, 1689, 1522, 1348, 1272, 1209, 1166, 1096, 767.
NMR δ(CDCl$_3$):

| | |
|---|---|
| 1.22 | (3H, t, J=7Hz, —CH$_2$CH$_3$) |
| 2.06 | (2H, quin, J=6Hz, —CH$_2$CH$_2$CH$_2$—) |
| 2.34 | (6H, s, —CH$_3$ × 2) |
| 4.07, 4.10 | (1H × 2, quin × 2, J=7Hz, —CH$_2$CH$_3$) |
| 4.15–4.40 | (8H, m, —COOCH$_2$CH$_2$CH$_2$OOC— and —OCH$_2$CH$_2$—N ) 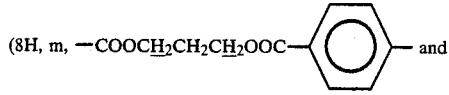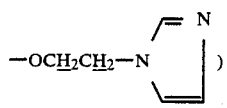 |
| 5.08 | (1H, s, C$_4$—H) |
| 6.40 | (1H, broad s, NH) 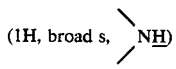 |
| 6.85 | (2H, d, J=9Hz, —O— —COO) 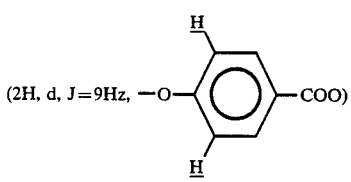 |
| 7.05, 7.08 | (1H × 2, s × 2, —N ) 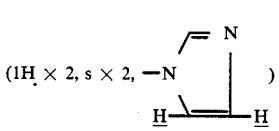 |
| 7.36 | (1H, t, J=8Hz, ) 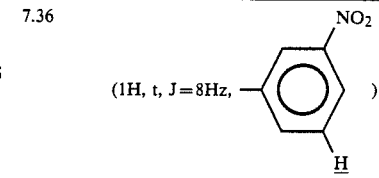 |
| 7.61 | (1H, s, —N ) 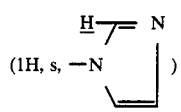 |
| 7.93 | (2H, d, J=9Hz, —O— —COO) 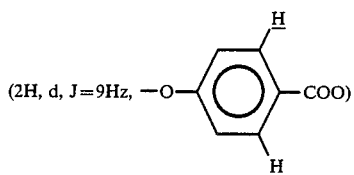 |
| 8.12 | (1H, t, J=2Hz, ) 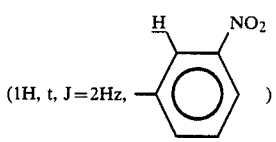 |

The free base was converted to its hydrochloride in an HCl-saturated ethanol. Upon recrystallization of from ethanol, 3-ethyl 5-[3-[4-[2-(1-imidazolyl)ethoxy]benzoyloxy]propyl]2,6-dimethyl-4-(3-nitrophenyl)-1,4-dihydropyridine-3,5-dicarboxylate hydrochloride was obtained as light-yellowish platy crystals (m.p. 147°–149° C.).

Molecular formula:
$C_{32}H_{34}N_4O_9\cdot HCl$
Appearance:
Light-yellowish platy crystals
(m.p. 147°–149° C.)
IR $\nu_{max}^{KBr}$cm$^{-1}$:
3393, 3063, 1705, 1523, 1486, 1350, 1270, 1201, 1168, 768
NMR δ(CDCl$_3$):

| | |
|---|---|
| 1.22 | (3H, t, J=7Hz, —CH$_2$CH$_3$) |
| 2.08 | (2H, broad quin, J=5Hz, —CH$_2$CH$_2$CH$_2$—) |
| 2.32, 2.39 | (3H × 2, s × 2, —CH$_3$ × 2) |
| 4.05, 4.07 | (1H × 2, quin × 2, J=7Hz, —CH$_2$CH$_3$) |
| 4.15–4.35 | (4H, m, —COOCH$_2$CH$_2$CH$_2$OOC— ) 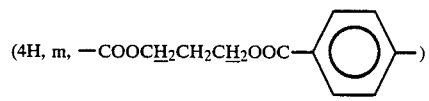 |
| 4.40–4.60 | (2H, broad m, —OCH$_2$CH$_2$—) |
| 4.75–4.85 | (2H, broad m, —OCH$_2$CH$_2$—N ) 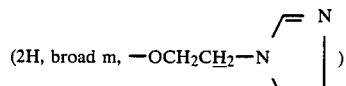 |
| 5.01 | (1H, s, C$_4$—H) |
| 6.66 | (1H, s, NH) 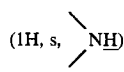 |

-continued

| | |
|---|---|
| 6.84 | (2H, d, J=9Hz, -O-C6H2H2-COO) |
| 7.33 | (1H, t, J=8Hz, nitrophenyl H) |
| 7.61 | (1H, d, J=8Hz, nitrophenyl H) |
| 7.88 | (2H, d, J=9Hz, -O-C6H2H2-COO) |
| 8.03 | (1H, t, J=2Hz, nitrophenyl H) |
| 7.38 | (2H, s, imidazolyl -N=CH-CH=) |
| 9.67 | (1H, s, imidazolyl H-C=N) |

-continued

| | |
|---|---|
| 1.00-1.94 | (16H, broad m, -(CH$_2$)$_8$-) |
| 2.26 | (2H, t, J=6.6Hz, -CH$_2$COO-) |
| 2.35, 2.37 | (3H × 2, s × 2, -CH$_3$ × 2) |
| 3.65 | (3H, s, -COOCH$_3$) |
| 3.96 | (2H, t, J=6.6Hz, -CH$_2$-N imidazolyl) |
| 4.26 | (4H, s, -COOCH$_2$CH$_2$OOC-) |
| 5.12 | (1H, s, C$_4$-H) |
| 6.96, 7.08 | (1H × 2, s × 2, -N imidazolyl H-C=C-H) |
| 7.16 | (1H, broad s, NH) |
| 7.40 | (1H, d, J=8Hz, nitrophenyl H) |
| 7.52 | (1H, s, -N imidazolyl H-C=N) |
| 7.68 | (1H, broad d, J=8Hz, nitrophenyl H) |
| 8.02 | (1H, broad d, J=8Hz, nitrophenyl H) |
| 8.14 | (1H, broad s, nitrophenyl H) |

EXAMPLES 7–22

The following compounds were prepared in the same manner as in Examples 1–6.

EXAMPLE 7

3-Methyl 5-[2-[11-(1-imidazolyl)undecanoyloxy]ethyl]2,6-dimethyl-4-(3-nitrophenyl)-1,4-dihydropyridine-3,5-dicarboxylate Molecular formula:
C$_{32}$H$_{42}$N$_4$O$_8$
Appearance:
Light-yellowish viscous oily substance
IR $\nu_{max}^{liq.film}$ cm$^{-1}$:
3507, 3321, 3180, 2924, 1734, 1700, 1648, 1523, 1502, 1347, 1211, 1114, 751
NMR δ(CDCl$_3$):

EXAMPLE 8

3-Methyl 5-[2-[3-[4-(1-imidazolylmethyl)-phenyl]acryloyloxy]ethyl]2,6-dimethyl-4-(3-nitrophenyl)-1,4-dihydropyridine-3,5-dicarboxylate Molecular formula:
C$_{31}$H$_{30}$N$_4$O$_8$
Appearance:
Yellowish amorphous powder
IR $\nu_{max}^{KBr}$ cm$^{-1}$:
3393, 2940, 1695, 1635, 1523, 1347, 1211, 1115, 747
NMR δ(CDCl$_3$):

| | |
|---|---|
| 2.34, 2.36 | (3H × 2, s × 2, -CH$_3$ × 2) |
| 3.60 | (3H, s, -COOCH$_3$) |
| 4.18-4.50 | (4H, broad m, -COOCH$_2$CH$_2$OOC-) |

-continued

| | |
|---|---|
| 5.08 | (1H, s, C$_4$—$\underline{H}$) |
| 5.14 | (2H, s, —C$\underline{H}_2$—N⟨imidazolyl⟩) |
| 6.32 | (1H, d, J=15Hz, —C$\underline{H}$=CH—phenyl) |
| 6.64 | (1H, broad s, ⟩N$\underline{H}$) |
| 6.90 | (1H, s, —N⟨imidazolyl⟩$\underline{H}$ or —N⟨imidazolyl⟩$\underline{H}$) |
| 7.88 | (1H, broad d, J=8Hz, ⟨nitrophenyl⟩) |
| 8.06 | (1H, broad s, ⟨nitrophenyl⟩) |

EXAMPLE 9

3-Methyl 5-[2-[3-(1-imidazolyl)-3-[4-(1-imidazolylmethyl)-phenyl]propionyloxy]ethyl]2,6-dimethyl-4-(3-nitrophenyl)-1,4-dihydropyridine-3,5-dicarboxylate Molecular formula:
C$_{34}$H$_{34}$N$_6$O$_8$
Appearance:
Yellowish amorphous powder
IR $\nu_{max}^{KBr}$cm$^{-1}$:
3327, 2940, 1734, 1687, 1652, 1522, 1348, 1210, 1115, 746
NMR δ(CDCl$_3$):

| | |
|---|---|
| 2.26, 2.34 | (3H × 2, s × 2, —C$\underline{H}_3$ × 2) |
| 3.16 | (2H, t, J=8Hz, —C$\underline{H}$—CH$_2$—) 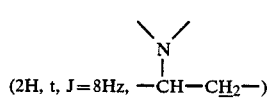 |
| 3.62 | (3H, s, —COOC$\underline{H}_3$) |
| 4.00–4.30 | (4H, broad m, —COOC$\underline{H}_2$C$\underline{H}_2$OOC—) |
| 5.07 | (1H, s, C$_4$—$\underline{H}$) |
| 5.10 | (2H, s, —C$\underline{H}_2$—N⟨imidazolyl⟩) 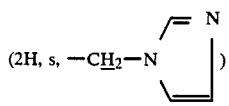 |

-continued

| | |
|---|---|
| 5.72 | (1H, t, J=8Hz, —C$\underline{H}$—CH$_2$—) |
| 6.90 | (2H, s, —N⟨imidazolyl⟩$\underline{H}$ or —N⟨imidazolyl⟩$\underline{H}$) |
| 7.94 | (1H, broad d, J=8Hz, ⟨nitrophenyl⟩) |
| 8.08 | (1H, broad s, ⟨nitrophenyl⟩) |

EXAMPLE 10

3-Methyl 5-[2-[4-[6-(1-imidazolyl)hexyloxy]benzoyloxy]ethyl]2,6-dimethyl-4-(3-nitrophenyl)-1,4-dihydropyridine-3,5-dicarboxylate Molecular formula:
C$_{34}$H$_{38}$N$_4$O$_9$
Appearance:
Yellowish amorphous powder
IR $\nu_{max}^{KBr}$cm$^{-1}$:
3330, 2921, 1695, 1640, 1523, 1346, 1271, 1206, 1090, 1015, 751
NMR δ(CDCl$_3$):

| | |
|---|---|
| 1.20–1.95 | (8H, m, —(CH$_2$)$_4$—) |
| 2.34, 2.36 | (3H × 2, s × 2, —C$\underline{H}_3$ × 2) |
| 3.60 | (3H, s, —COOC$\underline{H}_3$) |
| 3.80–4.10 | (4H, m, —OC$\underline{H}_2$—(CH$_2$)$_4$—C$\underline{H}_2$—N⟨imidazolyl⟩) 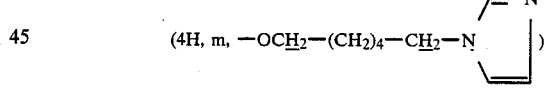 |
| 4.20–4.60 | (4H, m, —COOC$\underline{H}_2$C$\underline{H}_2$OOC—) |
| 5.10 | (1H, s, C$_4$—$\underline{H}$) |
| 6.92, 7.06 | (1H × 2, s × 2, —N⟨imidazolyl⟩) 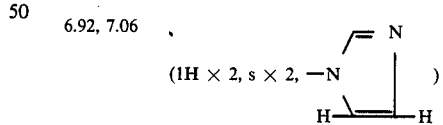 |
| 7.86 | (1H, broad d, J=8Hz, ⟨nitrophenyl⟩) 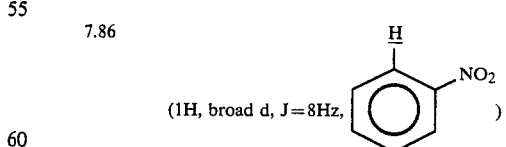 |
| 8.10 | (1H, broad s, ⟨nitrophenyl⟩) 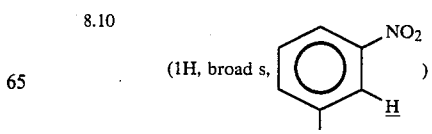 |

EXAMPLE 11

3-Methyl 5-[2-[2-methyl-3-[4-(3-pyridylmethyl)phenyl]acryloyloxy]ethyl]2,6-dimethyl-4-(3-nitrophenyl)-1,4-dihydropyridine-3,5-dicarboxylate Molecular formula: C₃₄H₃₃N₃O₈
Appearance: Yellowish amorphous powder
IR ν$_{max}^{KBr}$cm⁻¹:
3335, 2939, 1699, 1644, 1525, 1347, 1208, 1113, 1093, 746
NMR δ(CDCl₃):

| 2.08 | 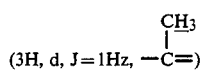 (3H, d, J=1Hz, —C=) |
| --- | --- |
| 2.36, 2.38 | (3H × 2, s × 2, —CH₃ × 2) |
| 3.60 | (3H, s, —COOCH₃) |
| 4.04 | 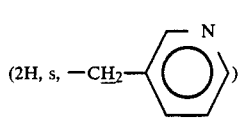 (2H, s, —CH₂—) |
| 4.20–4.52 | (4H, broad m, —COOCH₂CH₂OOC—) |
| 5.14 | (1H, s, C₄—H) |
| 6.24 | 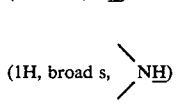 (1H, broad s, NH) |
| 7.96 | 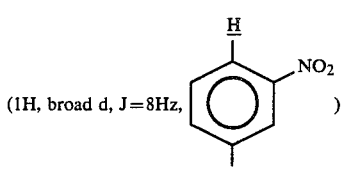 (1H, broad d, J=8Hz) |
| 8.12 | 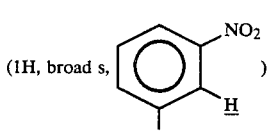 (1H, broad s) |
| 8.44–8.60 | 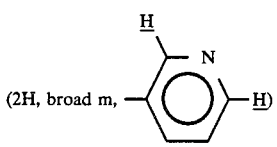 (2H, broad m) |

EXAMPLE 12

3-Methyl 5-[2-[2-methyl-3-[4-(3-pyridylmethyl)phenyl]acryloyloxy]ethyl]2,6-dimethyl-4-(2-nitrophenyl)-1,4-dihydropyridine-3,5-dicarboxylate Molecular formula: C₃₄H₃₃N₃O₈
Appearance: Yellowish amorphous powder
IR ν$_{max}^{KBr}$cm⁻¹:
3397, 1699, 1630, 1527, 1490, 1350, 1207, 1106, 750, 710
NMR δ(CDCl₃):

| 2.03 | 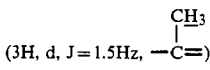 (3H, d, J=1.5Hz, —C=) |
| --- | --- |
| 2.29, 2.36 | (3H × 2, s × 2, —CH₃ × 2) |
| 3.53 | (3H, s, —COOCH₃) |
| 4.01 | 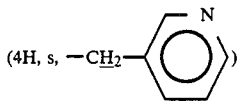 (4H, s, —CH₂—) |
| 4.20–4.45 | (4H, broad m, —COOCH₂CH₂OOC—) |
| 5.79 | (1H, s, C₄—H) |
| 6.59 | 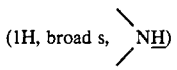 (1H, broad s, NH) |
| 8.42–8.55 | 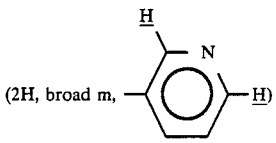 (2H, broad m) |

EXAMPLE 13

3-Methyl 5-[2-[4-[2-(1-imidazolyl)ethoxy]benzoyloxy]ethyl]2,6-dimethyl-4-(2-nitrophenyl)-1,4-dihydropyridine-3,5-dicarboxylate Molecular formula: C₃₀H₃₀N₄O₉
Appearance: Yellowish amorphous powder
IR ν$_{max}^{KBr}$cm⁻¹:
3330, 2942, 1694, 1604, 1526, 1353, 1271, 1248, 1209, 1104, 767
NMR δ(CDCl₃):

| 2.29, 2.34 | (3H × 2, s × 2, —CH₃ × 2) |
| --- | --- |
| 3.55 | (3H, s, —COOCH₃) |
| 4.25–4.45 | (8H, m, —COOCH₂CH₂OOC— and —OCH₂CH₂N<) |
| 5.77 | (1H, s, C₄—H) |
| 6.32 | 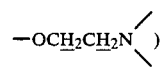 (1H, broad s, NH) |
| 6.84 | 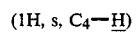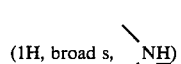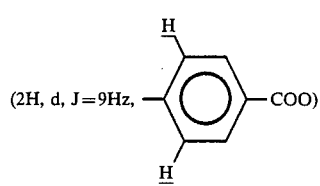 (2H, d, J=9Hz, —COO) |
| 7.05, 7.08 | 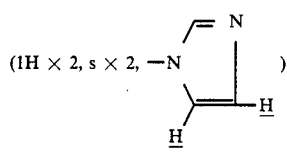 (1H × 2, s × 2, —N) |
| 7.61 | 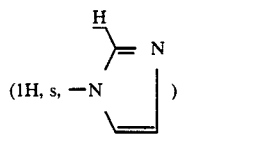 (1H, s, —N) |

| | |
|---|---|
| 7.87 | (2H, d, J=9Hz, H—⌬—O—H) |

EXAMPLE 14

3-Methyl 5-[2-[3-[4-(1-imidazolylmethyl)phenyl]acryloyloxy]ethyl]2,6-dimethyl-4-(2-fluorophenyl)-1,4-dihydropyridine-3,5-dicarboxylate Molecular formula: C₃₁H₃₀FN₃O₆
Appearance: Light-yellowish amorphous powder
IR $\nu_{max}^{KBr}$ cm⁻¹:
3402, 2939, 1692, 1635, 1490, 1305, 1210, 1114, 756
NMR δ(CDCl₃):

| | |
|---|---|
| 2.32, 2.34 | (3H × 2, s × 2, —CH₃ × 2) |
| 3.56 | (3H, s, —COOCH₃) |
| 4.10–4.50 | (4H, broad m, —COOCH₂CH₂OOC—) |
| 5.16 | (2H, s, —CH₂—N⟨imidazole⟩) |
| 5.28 | (1H, s, C₄—H) |
| 6.38 | (1H, d, J=16Hz, —CH=CH—⌬—) |
| 6.39 | (1H, broad s, ⟩NH) |
| 6.95, 7.14 | (1H × 2, s × 2, —N⟨imidazole⟩) |
| 7.64 | (1H, d, J=16Hz, —CH=CH—⌬—) |

EXAMPLE 15

3-Methyl 5-[2-[3-[4-(1-imidazolymethyl)phenyl]acryloyloxy]ethyl]2,6-dimethyl-4-(2,3-dichlorophenyl)-1,4-dihydropyridine-3,5-dicarboxylate Molecular formula: C₃₁H₂₉Cl₂N₃O₆
Appearance: Light-yellowish amorphous powder
IR $\nu_{max}^{KBr}$ cm⁻¹:
3406, 2917, 1693, 1635, 1496, 1304, 1274, 1207, 1134, 750
NMR δ(CDCl₃):

| | |
|---|---|
| 2.26, 2.32 | (3H × 2, s × 2, —CH₃ × 2) |
| 3.56 | (3H, s, —COOCH₃) |
| 4.20–4.50 | (4H, b.m, —COOCH₂CH₂OOC—) |
| 5.16 | (2H, s, —CH₂—N⟨imidazole⟩) |
| 5.48 | (1H, s, C₄—H) |
| 6.36 | |
| 6.36 | (1H, d, J=16Hz, —CH=CH—⌬—) |
| 6.64 | (1H, broad s, ⟩NH) |
| 6.92 | (1H, s, —N⟨imidazole⟩H or —N⟨imidazole⟩H) |

EXAMPLE 16

3-Methyl 5-[2-[4-[2-(1-imidazolyl)ethoxy]-benzoyloxy]ethyl]2,6-dimethyl-4-(2,3-dichlorophenyl)-1,4-dihydropyridine-3,5-dicarboxylate Molecular formula: C₃₀H₂₉Cl₂N₃O₇
Appearance: Colorless amorphous powder
IR $\nu_{max}^{KBr}$ cm⁻¹:
3405, 2938, 1693, 1644, 1623, 1505, 1418, 1303, 1247, 1208, 1134, 1050, 770
NMR δ(CDCl₃):

| | |
|---|---|
| 2.28 | (6H, s, —CH₃ × 2) |
| 3.56 | (3H, s, —COOCH₃) |
| 4.20–4.50 | (8H, m, —COOCH₂CH₂OOC— and —OCH₂CH₂—N⟨imidazole⟩) |
| 5.48 | (1H, s, C₄—H) |
| 6.36 | (1H, broad s, ⟩NH) |
| 6.86 | 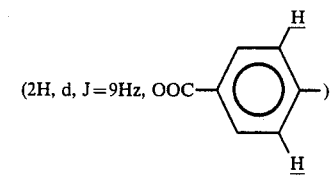 (2H, d, J=9Hz, OOC—⌬—) |
| 7.62 | 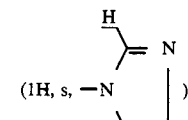 (1H, s, —N⟨imidazole⟩) |

-continued 7.90  (2H, d, J=9Hz, 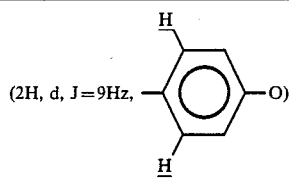)

EXAMPLE 17

3-Methyl 5-[2-[3-(1-imidazolyl)-3-[4-(1-imidazdolylmethyl)-phenyl]propionyloxy]ethyl]2,6-dimethyl-4-(2,3-dichlorophenyl)-1,4-dihydropyridine-3,5-dicarboxylate Appearance: Colorless amorphous powder
IR $\nu_{max}^{KBr}$cm$^{-1}$:
3261, 2942, 1734, 1688, 1640, 1499, 1376, 1209, 1109, 750

NMR δ(CDCl$_3$):

| | |
|---|---|
| 2.30 | (6H, s, —C$\underline{H}_3$ × 2) |
| 3.16 | (2H, d, J=8Hz, —C$\underline{H}$—C$\underline{H}_2$—) 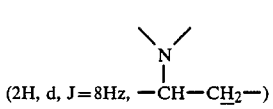 |
| 3.58 | (3H, s, —COOC$\underline{H}_3$) |
| 4.00–4.34 | (4H, broad m, —COOC$\underline{H}_2$C$\underline{H}_2$OOC—) |
| 5.12 | (2H, s, —C$\underline{H}_2$N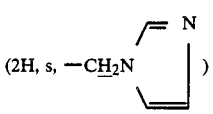) |
| 5.44 | (1H, s, C$_4$—$\underline{H}$) |
| 5.64 | (1H, t, J=8Hz, —C$\underline{H}$—) 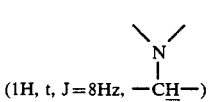 |
| 6.92 | (2H, broad s, —N 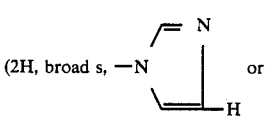 or —N 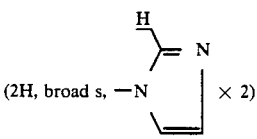 × 2) |
| 7.56 | (2H, broad s, —N 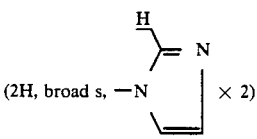 × 2) |
| 8.08 | (1H, broad s, N$\underline{H}$) 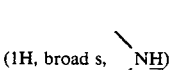 |

EXAMPLE 18

3-Ethyl 5-[3-[3-[4-(1-imidazolylmethyl)phenyl]acryloyloxy]-propyl]2,6-dimethyl-4-(3-nitrophenyl)-1,4-dihydropyridine-3,5-dicarboxylate Molecular formula: C$_{33}$H$_{34}$N$_4$O$_8$
Appearance: Yellowish amorphous powder
IR $\nu_{max}^{KBr}$cm$^{-1}$:
3323, 2921, 1693, 1635, 1523, 1347, 1206, 1114, 744

NMR δ(CDCl$_3$):

| | |
|---|---|
| 1.23 | (3H, t, J=6Hz, —CH$_2$C$\underline{H}_3$) |
| 1.80–2.10 | (2H, m, —CH$_2$C$\underline{H}_2$CH$_2$—) |
| 2.33, 2.36 | (3H × 2, s × 2, —C$\underline{H}_3$ × 2) |
| 3.90–4.30 | (6H, m, —COOC$\underline{H}_2$CH$_3$ and —COOC$\underline{H}_2$CH$_2$C$\underline{H}_2$OOC—) |
| 5.10 | (1H, s, C$_4$—$\underline{H}$) |
| 5.14 | (2H, s, —C$\underline{H}_2$—N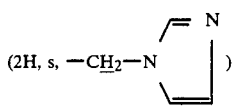) |
| 6.20 | (1H, broad s, N$\underline{H}$) 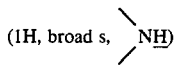 |
| 6.38 | (1H, d, J=16Hz, —C$\underline{H}$=CH—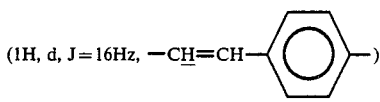) |
| 6.90 | (1H, s, —N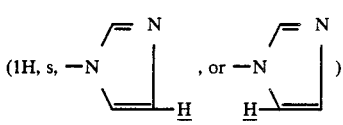, or —N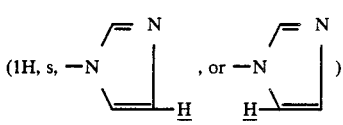) |
| 8.00 | (1H, b.d, J=8Hz, 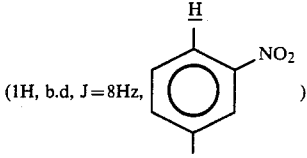) |
| 8.13 | (1H, broad s, 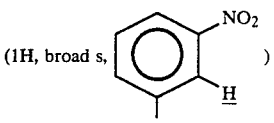) |

EXAMPLE 19

3-Methyl 5-[2-[3-[4-(1-imidazolylmethyl)phenyl]acryloyloxy]-ethyl]2,6-dimethyl-4-(2-nitrophenyl)-1,4-dihydropyridine-3,5-dicarboxylate Molecular formula: C$_{31}$H$_{30}$N$_4$O$_8$
Appearance: Yellowish amorphous powder
IR $\nu_{max}^{KBr}$cm$^{-1}$:
3333, 2940, 1694, 1636, 1526, 1307, 1208, 1110, 782

NMR δ(CDCl$_3$):

| | |
|---|---|
| 2.30, 2.37 | (3H × 2, s × 2, —C$\underline{H}_3$ × 2) |
| 3.53 | (3H, s, COOC$\underline{H}_3$) |
| 4.20–4.40 | (4H, m, —COOC$\underline{H}_2$C$\underline{H}_2$OOC—) |

-continued

| | |
|---|---|
| 5.16 | (2H, s, —C<u>H</u>₂—N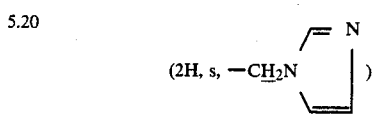) |
| 5.79 | (1H, s, C₄—<u>H</u>) |
| 6.10 | (1H, broad s, \N<u>H</u>/) |
| 6.33 | (1H, d, J=16Hz, —C<u>H</u>=CH—⌬—) |
| 6.92, 7.11 | (1H × 2, broad s × 2, —N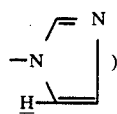) |

EXAMPLE 20

3-Methyl 5-[2-[3-[4-(1-imidazolylmethyl)phenyl]acryloyloxy]ethyl]2,6-dimethyl-4-(2-trifluoromethylphenyl)-1,4-dihydropyridine-3,5-dicarboxylate Molecular formula: $C_{32}H_{30}F_3N_3O_6$
Appearance: Light-yellowish amorphous powder
IR $\nu_{max}^{KBr}$ cm$^{-1}$:
3332, 2939, 1695, 1635, 1497, 1307, 1209, 1112, 761
NMR δ(CDCl₃):

| | |
|---|---|
| 2.30, 2.34 | (3H × 2, s × 2, —C<u>H</u>₃ × 2) |
| 3.56 | (3H, s, —COOC<u>H</u>₃) |
| 4.00–4.50 | (4H, m, —COOC<u>H</u>₂CH₂OOC—) |
| 5.20 | (2H, s, —C<u>H</u>₂N ) |
| 5.62 | (1H, broad s, C₄—<u>H</u>) |
| 6.38 | (1H, broad s, \N<u>H</u>) |
| 6.40 | (1H, d, J=16Hz, —C<u>H</u>=CH—⌬—) |
| 6.98 | (1H, broad s, —N , or  —N ) |

EXAMPLE 21

3-Ethyl 5-[2-[3-(1-imidazolyl)-3-[4-(1-imidazolylmethyl)phenyl]propionyloxy]ethyl]2,6-dimethyl-4-(3-nitrophenyl)-1,4-dihydropyridine-3,5-dicarboxylate Molecular formula: $C_{36}H_{38}N_6O_8$
Appearance: Yellowish viscous oily substance
IR $\nu_{max}^{liq.film}$ cm$^{-1}$:
3268, 2970, 1732, 1685, 1522, 1348, 1200, 1113, 750
NMR δ(CDCl₃):

| | |
|---|---|
| 2.22 | (3H, t, J=7Hz, —CH₂C<u>H</u>₃) |
| 1.84 | (2H, broad t, J=6Hz, —COOCH₂C<u>H</u>₂CH₂OOC—) |
| 2.34 | (6H, s, —C<u>H</u>₃ × 2) |
| 3.22 | (2H, d, J=8Hz, —CH—C<u>H</u>₂COO—) |
| 3.70–4.30 | (6H, m, —C<u>H</u>₂CH₃ and —COOC<u>H</u>₂CH₂CH₂OOC—) |
| 5.10 | (1H, s, C₄—<u>H</u>) |
| 5.16 | (2H, s, —C<u>H</u>₂—N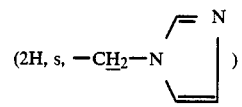) |
| 5.78 | (1H, t, J=8Hz, —CH₂C<u>H</u>—) 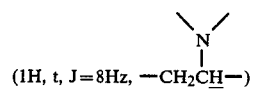 |
| 6.96, 7.00 | (1H × 2, s × 2, —N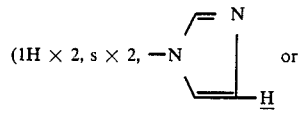 or —N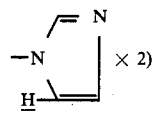 × 2) |
| 8.02 | (1H, broad d, J=8Hz, 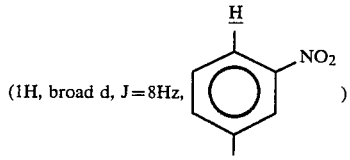) |
| 8.10 | (1H, broad s, \N<u>H</u>) |
| 8.18 | (1H, broad s, 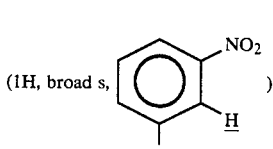) |

EXAMPLE 22

3-Methyl 5-[2-[3-(1-imidazolyl)-3-[4-(1-imidazolylmethyl)phenyl]propionyloxy]ethyl]2,6-dimethyl-4-(2-trifluoromethylphenyl)-1,4-dihydropyridine-3,5-dicarboxylate Molecular formula: $C_{35}H_{34}F_3N_5O_6$
Appearance: Light-yellowish amorphous powder
IR $\nu_{max}^{KBr}$ cm$^{-1}$:
3366, 1734, 1690, 1407, 1308, 1210, 1112, 764
NMR $\delta$(CDCl$_3$):

| | |
|---|---|
| 2.30 | (6H, s, $-C\underline{H}_3 \times 2$) |
| 3.14 | (2H, d, J=8Hz, $-CHC\underline{H}_2COO-$) |
| 3.58 | (3H, s, $-COOC\underline{H}_3$) |
| 3.90–4.40 | (4H, m, $-COOC\underline{H}_2C\underline{H}_2OOC-$) |
| 5.14 | (2H, s, $-C\underline{H}_2N$ imidazolyl) |
| 5.58 | (1H, broad s, C$_4$—$\underline{H}$) |
| 5.74 | (1H, t, J=8Hz, $-CH_2C\underline{H}-$) |
| 6.94 | (2H, broad s, imidazolyl) |
| 3.47 | (2H, s, $CH_3\overset{O}{\underset{\|}{C}}-C\underline{H}_2-COO-$) |
| 4.27 | (2H, t, J=5Hz, phenyl-$OC\underline{H}_2-$) |
| 4.32 | (2H, t, J=6.2Hz, $CH_3\overset{O}{\underset{\|}{C}}CH_2COOC\underline{H}_2-$) |
| 4.37 | (2H, t, J=5Hz, $-C\underline{H}_2-N$ imidazolyl) |
| 4.38 | (2H, t, J=6.2Hz, $-C\underline{H}_2OOC-$phenyl) |
| 6.89 | (2H, d, J=8.9Hz, OOC-phenyl-O-) |
| 7.05, 7.08 | (1H × 2, t × 2, J=1.2Hz, imidazolyl) |
| 7.60 | (1H, broad s, imidazolyl) |
| 7.98 | (2H, d, J=8.9Hz, $-OOC-$phenyl) |

EXAMPLE 23

3-Ethyl 5-[3-[4-[2-(1-imidazolyl)ethoxy]benzoyloxy]propyl]2,6-dimethyl-4-(3-nitrophenyl)-1,4-dihydropyridine-3,5-dicarboxylate (1) After adding at room temperature 4.1 ml of diketene dropwise to 10 g of 3-hydroxypropyl 4-[2-(1-imidazolyl)ethoxy]benzoate dissolved in 300 ml of chloroform, the resultant mixture was stirred for further 18 hours. The reaction mixture was concentrated under reduced pressure, and the residue was purified by silica gel column chromatography to obtain 10.1 g of 3-[4-[2-(1-imidazolyl)ethoxy]benzoyloxy]propyl acetoacetate as colorless crystals (m.p. 49.5°–51.5° C.; yield: 78%)

IR $\nu_{max}^{KBr}$ cm$^{-1}$:
3410, 1700, 1275, 1250, 1170
NMR $\delta$(CDCl$_3$):
2.12 (2H, quin, J=6.2Hz, $-CH_2C\underline{H}_2CH_2-$)
2.27 (3H, s, $-\overset{O}{\underset{\|}{C}}-C\underline{H}_3$)

(2) Added to 5 g of the above-obtained acetoacetate dissolved in 50 ml of benzene were 2.1 g of 3-nitrobenzaldehyde and 0.5 ml of piperidine. After fitting a Dean-Stark water separator, the mixture was refluxed for 2 hours. Ethyl acetate was added to the reaction mixture. After washing the organic layer with brine, the organic layer was dried. The solvents were distilled off, and the residue was purified by silica gel column chromatography to obtain 5.7 g of 3-[4-[2-(1-imidazolyl)ethoxy]benzoyloxy]propyl 2-(3-nitrobenzylidene)acetoacetate as a mixture of its E-isomer and Z-isomer (yield: 84%).

(3) To 7.34 g of the benzylidene derivative dissolved in 25 ml of isopropanol, 2 ml of ethyl 3-aminocrotonate was added. The resultant mixture was refluxed with stirring at 85° C. for 3 hours. After allowing the reaction mixture to cool down, it was concentrated under reduced pressure and the residue was purified by silica gel column chromatography, thereby obtaining 7.19 g of 3-ethyl 5-[3-[4-[2-(1-imidazolyl)ethoxy]benzoyloxy]- propyl 2,6-dimethyl-4-(3-nitrophenyl)-1,4-dihydropyridine-3,5-dicarboxylate (the compound of Example 6) (yield: 80%).

EXAMPLE 24

After adding 0.11 ml of ethyl acetoacetate and 0.06 ml of conc. aqueous ammonia to a solution which contained 382 mg of 3-[4-[2-(1-imidazolyl)ethoxy]benzoyloxy]propyl 2-(3-nitrobenzylidene)acetoacetate, which had been obtained in Example 23(2), dissolved in 4 ml of isopropanol, the resultant mixture was stirred at 80° C. for 3.5 hours. After allowing the reaction mixture to cool down, it was concentrated under reduced pressure and the residue was purified by silica gel column chromatography to obtain 127 mg of the compound of Example 6 as yellowish powder (yield: 27%).

EXAMPLE 25

To a solution containing 186 mg of 3-[4-[2-(1-imidazolyl)ethoxy]benzoyloxy]propyl acetoacetate, which had been obtained in Example 23(1), in 2 ml of isopropanol, were added 76 mg of 3-nitrobenzaldehyde and 0.07 ml of ethyl 3-aminocrotonate. The resultant mixture was refluxed with stirring at 85° C. for 4.5 hours. After allowing the reaction mixture to cool down, it was concentrated under reduced pressure and the residue was purified by silica gel column chromatography to obtain 261 mg of the compound of Example 6 as yellowish powder (yield: 85%).

EXAMPLE 26

Added to a solution of 309 mg of 3-[4-[2-(1-imidazolyl)ethoxy]benzoyloxy]propyl acetoacetate, which had been obtained in Example 23(1), in 3 ml of ethanol were 139 mg of 3-nitrobenzaldehyde, 0.12 ml of ethyl acetoacetate and 0.075 ml of conc. aqueous ammonia. The resultant mixture was refluxed with stirring at 80° C. for 5 hours, followed by a further addition of 0.05 ml of conc. aqueous ammonia. The resultant mixture was refluxed with stirring for further 1 hour. After allowing the reaction mixture to cool down, it was concentrated under reduced pressure and the thus-obtained residue was purified by silica gel column chromatography to obtain 292 mg of the compound of Example 6 as yellowish powder (yield: 57%).

We claim:

1. A 1,4-dihydropyridine-3,5-dicarboxylate compound represented by the following general formula (I):

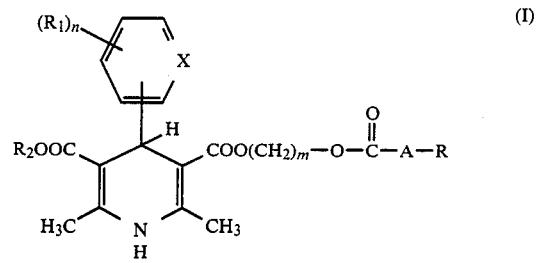

wherein R means an imidazolyl or pyridyl group, $R_1$ denotes a hydrogen or halogen atom or a nitro or trifluoromethyl group, $R_2$ is a lower alkyl group, X is CH or N, A means a lower alkylene group,

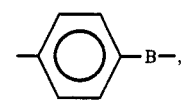

B being a lower alkylene or O-lower alkylene group,

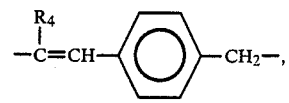

$R_4$ being a hydrogen atom or lower alkyl group, or

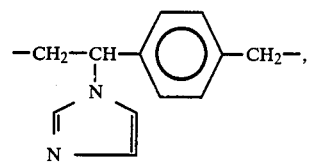

m denotes a number of 1–3, and n stands for 1 or 2.

2. An anti-arteriosclerotic pharmaceutical composition comprising an effective amount of the compound of claim 1 in association with a pharmaceutically acceptable carrier.

3. A method of treating arteriosclerosis in a subject in need of such treatment which comprises administering an effective amount of the compound of claim 1 to said subject.

* * * * *